United States Patent [19]

Jessel, Jr. et al.

[11] Plant 4,188

[45] Jan. 17, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 732,190

[22] Filed: Oct. 13, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum cultivar having daisy type inflorescence, nine week flowering response, short plant height, lavender-pink ray floret color, and production capabilities under high light flowering periods.

3 Drawing Figures

The present invention comprises a new and distinct cultivar of *Chrysanthemum morifolium*, Ramat., hereinafter referred to by the cultivar name Circus (#72261002).

Circus is a product of a planned breeding program which had the objective of creating new chrysanthemum cultivars with daisy type inflorescence, with 8 or 9 week flowering response, with short plant height, with lavender-pink ray floret color, and the ability to produce commercially acceptable quality as a pot plant during high light flowering periods. These traits in combination were not present in previously available commercial cultivars.

Circus was originated from a cross made in a controlled breeding program in Barberton, Ohio in 1971. The female, or seed parent, was #71078020 (unnamed seedling), a lavender-pink daisy. The male, or pollen parent, was #71078021 (unnamed seedling), a red-bronze daisy. Both #71078020 and #71078021 were originated by the present inventors in 1970 from a cross between Dramatic (#67079001; U.S. Plant Pat. No. 3,189) and Mischief (#22019E01; unpatented; commercially available).

Circus was discovered and selected as a flowering plant within the progeny of the stated cross by Walter H. Jessel, Jr. and William E. Duffett on Oct. 26, 1972 in a controlled environment in Barberton, Ohio.

The first act of asexual reproduction of Circus was accomplished when vegetative cuttings were taken from the initial selection in January, 1973 in a controlled environment in Barberton, Ohio by a technician working under formulations established and supervised by Walter H. Jessel, Jr. and William E. Duffett. Horticultural examination of selected units initiated Aug. 2, 1973 has demonstrated that the combination of characteristics as herein disclosed for Circus are firmly fixed and are retained through successive generations of asexual reproduction.

Circus has not been observed under all possible environmental conditions. The phenotype may vary significantly with variations in environment such as temperature, light intensity, and daylength. The following observations, measurements and comparisons describe plants grown in Barberton, Ohio under greenhouse conditions which closely approximate those generally used in commercial practice, as described in Chart A which appears at the end of the present specification. A light intensity chart of general use is shown in ASHAE Trans., Vol. 64, pg. 64, and reference is made thereto.

The following traits have been repeatedly observed and are determined to be basic characteristics of Circus which in combination distinguish this chrysanthemum as a new and distinct cultivar:

1. Flat inflorescence form.
2. Daisy inflorescence type.
3. Lavender-pink floret color, with minimum color oxidation.
4. Yellow-green (immature) to yellow (mature) disc floret color.
5. Uniform 9 week flowering response to photoperiodic short day control.
6. Diameter across face of inflorescence up to 70 mm. at maturity.
7. Medium plant height (requiring 1 to 2 long day weeks prior to short days and one application 2500 ppm. B-9 SP 14 to 21 days after the beginning of short days to attain a flowered plant height of 30 to 45 cm.)
8. Semi-spreading branching pattern.

The accompanying photographic drawings show typical inflorescence and foliage characteristics of Circus. Sheet 1 is a color photograph of Circus. Sheet 2 is a black and white photograph showing three views of the inflorescence of Circus. Sheet 3 is a black and white photograph showing the foliage of Circus at three stages of growth.

Of the many commercial cultivars known to the present inventors, the most similar existing cultivar in comparison to Circus is Gem (#70038041; U.S. Plant Pat. No. 3,740). Reference is made to attached Chart B which compares certain characteristics of Circus and Gem. It will be noted that Circus has darker ray floret color, smaller diameter across face of inflorescence, longer flowering response, shorter plant height and more spreading branching pattern. The inflorescence form and inflorescence type of Gem are similar to those same characteristics of Circus.

In the following description, color references are made to The Munsell Limit Color Cascade, 1972 edition. The color values were determined between 10:00 and 10:30 A.M. on June 24, 1976 under 150 foot-candle light intensity at Barberton, Ohio.

Botanical classification: *Chrysanthemum morifolium*, Ramat., cv Circus.

INFLORESCENCE (see Sheets 1 and 2 of drawings).

Capitulum:

*Form.*—Flat.

*Type.*—Daisy.

*Permanence.*—14 to 18 days.

*Diameter across face.*—57 to 70 mm.

Corolla of ray florets:

*Color (abaxial).*—45 to 46-5.

*Color (adaxial).*—45-4 to 46-2.

Corolla of disc florets:

*Color (immature.*—22-12.

*Color (mature).*—28-9.

Reproductive organs:

*Gynoecium.*—Present both disc and ray florets.

*Androecium.*—Present disc florets only; moderate pollen.

PLANT (see Sheet 1 of drawings)

General appearance: semi-spreading branching pattern; medium height.

Foliage (see Sheets 1 and 3 of drawings.)

*Color (abaxial).*—20-15.

*Color (adaxial).*—Approximately 20-15 overlaid with white.

CHART A

AVERAGE GREENHOUSE CHRYSANTHEMUM ENVIRONMENTS FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off-7:30 AM | From Oct. 15 300 ppm |
| WINTER | 58° F to 62° F | 65° F to 70° F | 60° F to 65°0 F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off-7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on-6:00 PM Off-8:00 AM | NONE |

CHART B

COMPARISON OF CIRCUS AND GEM

| CULTIVAR | RAY FLORET COLOR | DIAMETER ACROSS FACE OF INFLORESCENCE | INFLORESCENCE FORM & TYPE | FLOWERING RESPONSE | PLANT HEIGHT | BRANCHING PATTERN |
|---|---|---|---|---|---|---|
| Circus | Lavender Pink | 57 to 70 mm. | Flat Daisy | 9 weeks | Medium | Semi-spreading |
| Gem | Light Lavender Pink | 70 to 89 mm. | Flat Daisy | 7 weeks | Tall | Semi-spreading |

COMPARISONS MADE OF PLANTS GROWN IN BARBERTON, OHIO UNDER CONDITIONS AS DESCRIBED IN CHART A.

We claim:

1. A new and distinct cultivar of *Chrysanthemum morifolium,* Ramat., known by the cultivar name Circus and particularly characterized as to uniqueness by the combined characteristics of flat inflorescence form; daisy inflorescence type; lavender-pink ray floret color, with minimum color oxidation; yellow-green (immature) to yellow (mature) disc floret color; uniform nine week flowering response to photographic short day control; diameter across face of inflorescence up to 70 mm. at maturity; medium plant height; and semi-spreading branching pattern.

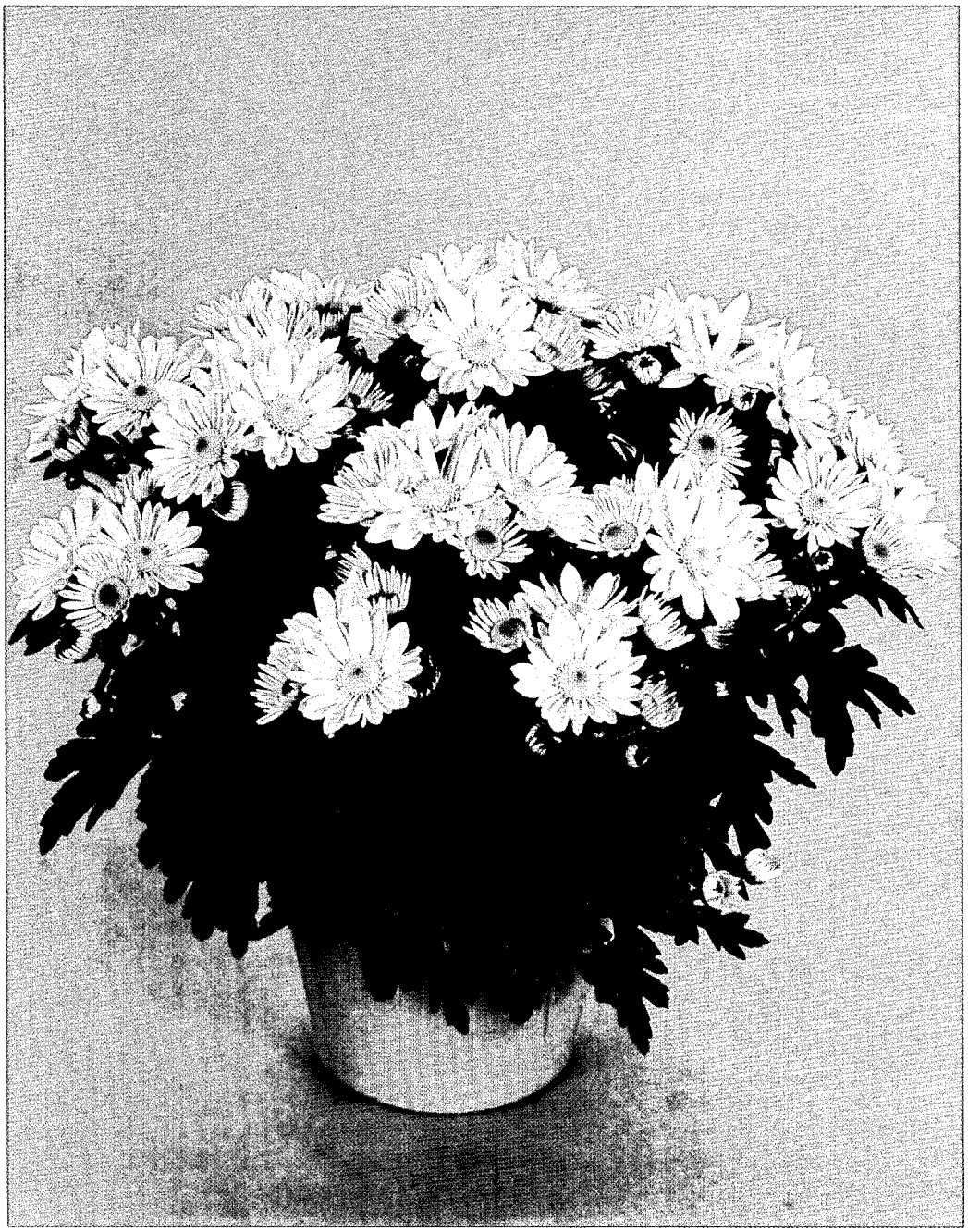

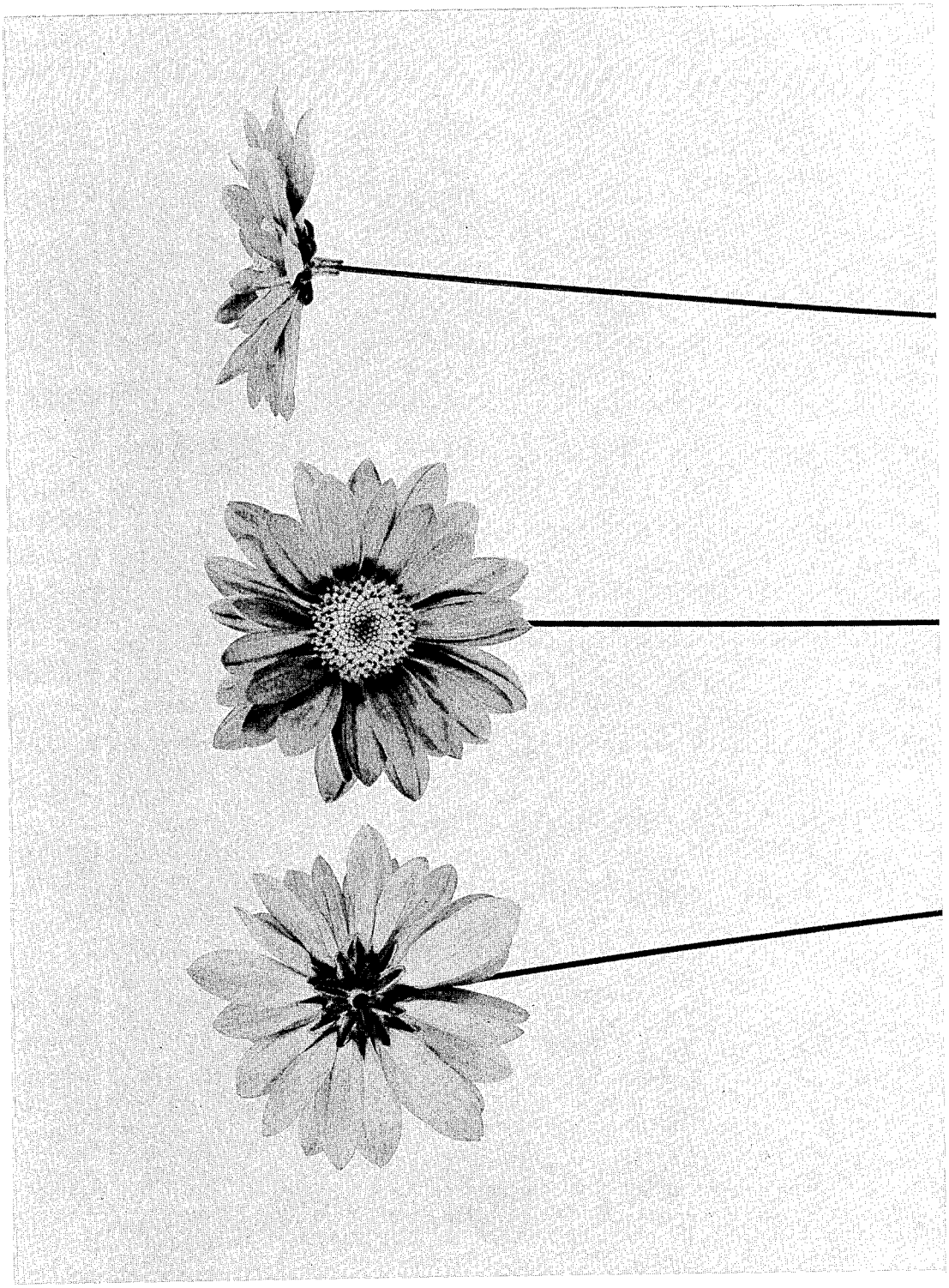

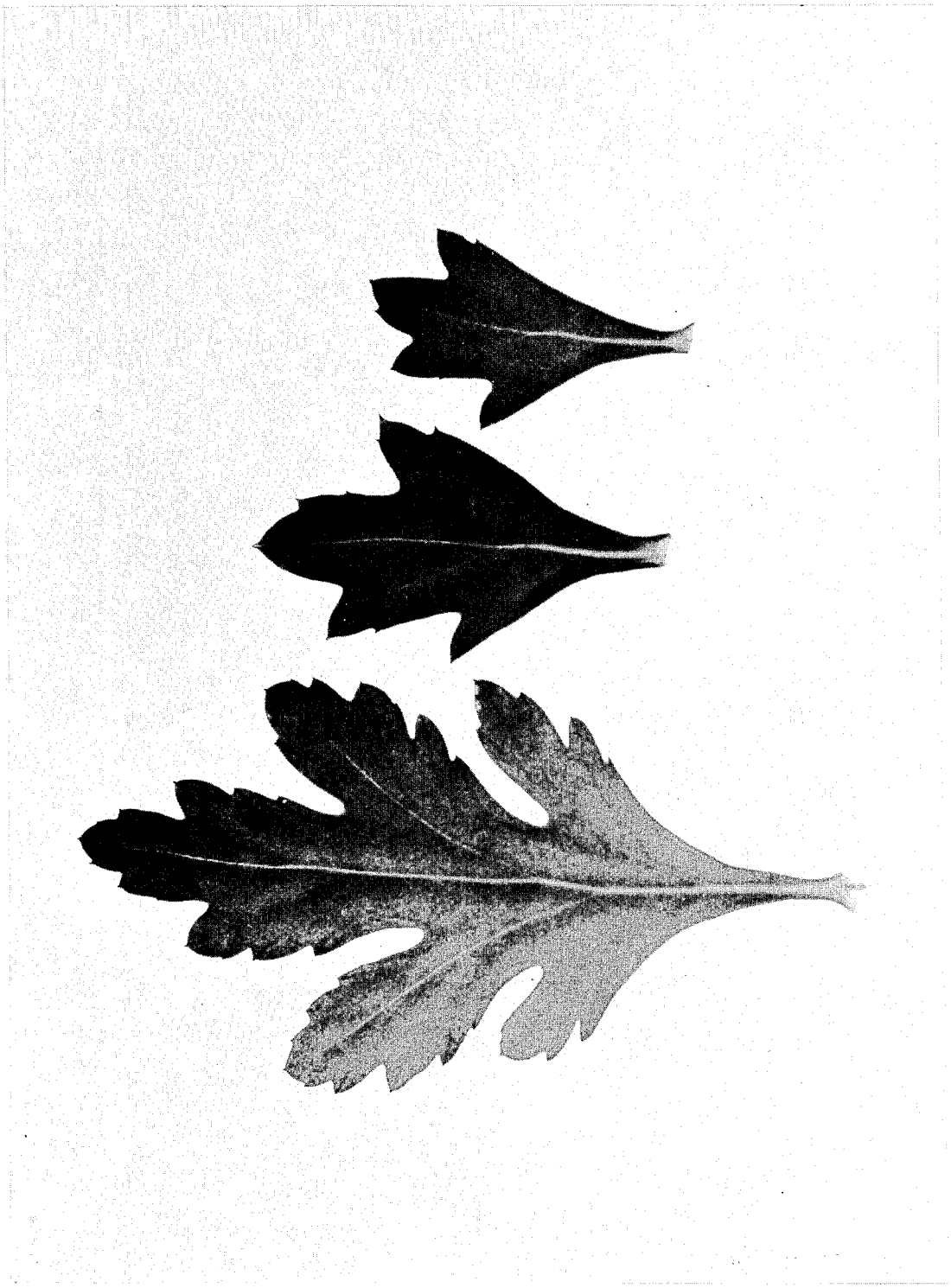

* * * * *